United States Patent [19]

Hennebert et al.

[11] Patent Number: 4,637,916
[45] Date of Patent: Jan. 20, 1987

[54] STERILIZATION METHOD EMPLOYING A CIRCULATING GASEOUS STERILANT

[75] Inventors: Pierre Hennebert, Brussels; Jean Gillard, Tourinnes-La-Grosse; Michel Roland, Brussels, all of Belgium

[73] Assignees: Universite Catholique de Louvain, Ottignies Louvain-la-Neuve; Manufacture Belge de Gembloux S.A., Gembloux, both of Belgium

[21] Appl. No.: 571,765

[22] Filed: Jan. 18, 1984

[30] Foreign Application Priority Data

Jan. 28, 1983 [BE] Belgium ................................. 895729

[51] Int. Cl.⁴ .......................... A01N 27/00; A61L 2/20
[52] U.S. Cl. ......................................... 422/36; 422/27; 422/295
[58] Field of Search ...................... 422/27, 33, 34, 36, 422/295, 305, 306, 297

[56] References Cited

U.S. PATENT DOCUMENTS 1,279,524 9/1918 Eckmann ........................ 422/36 X
2,397,292 3/1946 Salle ................................. 422/36 X
3,958,935 5/1976 Kowol .............................. 422/36
4,004,024 1/1977 Eggensberger et al. ......... 424/285
4,040,977 8/1977 Eggensberger et al. ......... 422/36 X
4,239,731 12/1980 Gillis et al. ....................... 422/34 X
4,410,492 10/1983 Kaye ................................. 422/34 X
4,447,394 5/1984 Krouthen ......................... 422/27

FOREIGN PATENT DOCUMENTS 2313484 10/1974 Fed. Rep. of Germany .
2921915 12/1980 Fed. Rep. of Germany .
2502498 10/1982 France ............................. 422/36
23954 of 1908 United Kingdom ............. 422/36
459721 1/1937 United Kingdom ............. 422/34

OTHER PUBLICATIONS

"Studies the Use of Low Concentration of Formaldehyde with Steam at Sub-Atmospheric Pressures as a Method of Sterilising Non-Porous Heat Sensitive Items", Weymes et al., Greater Glasgow Health Board Sterilization Center, Aug. 1975.
Pickerill, J. K., "Practical System for Steam-Formaldehyde Sterilizing", Lab. Pract. (GB); vol. 24; No. 6; 6/75; pp. 401-404.

Primary Examiner—David L. Lacey
Assistant Examiner—Brion P. Heaney
Attorney, Agent, or Firm—Beveridge, DeGrandi & Weilacher

[57] ABSTRACT

A sterilization method comprising subjecting a sterilization chamber to an initial vacuum and then introducing steam to increase chamber pressure. The introduction of steam is interrupted and the chamber is brought into communication with a solution in a gaseous sterilant generator. The mixture of gaseous sterilant and chamber atmosphere are continuously circulated whereby equilibrium is established and the material to be sterilized is subject to constant temperature, pressure, sterilant concentration, and relative humidity for a period of time sufficient for sterilization. Also disclosed is an apparatus capable of performing the sterilization method comprising a sterilization chamber in combination with a gaseous sterilant generator. Formaldehyde is the preferred sterilizing agent.

6 Claims, 6 Drawing Figures

STERILIZATION METHOD EMPLOYING A CIRCULATING GASEOUS STERILANT

BACKGROUND OF THE INVENTION

The present invention relates to a process for the sterilization of one or more chemical products in a gaseous state for use in the treatment of materials, articles or enclosures.

Recourse to gaseous sterilization is essential for sterilizing products or articles which cannot be subjected to the elevated temperatures employed in conventional heat sterilization methods, or to high energy radiation, such as gamma rays, or to germicidal solutions, such as glutaraldehyde solutions. In general, gas sterilization is mainly carried out by exposing the surfaces to be sterilized to biocidal gases such as ethylene oxide or formaldehyde. The processes employed at present have many disadvantages.

Ethylene oxide, which is employed on a very large scale, reacts slowly and is highly inflammable. It is, moreover, highly toxic, being capable of producing mutagenic effects in exposed individuals. It has to be employed at elevated concentrations (from 500 to 2,000 mg per liter) which exacerbate the hazard, such as the presence of residues in the articles, high concentrations in the atmosphere of sterilization rooms, and environmental pollution.

Formaldehyde, whose biocidal activity has long been known, presents significantly fewer hazards than ethylene oxide, but the results obtained in the processes currently employed are highly unsatisfactory. Although, in some working conditions, sterilization cycles have been found to be effective against populations of resistant spores (*B. Subtilis, B. stearothermophilus*) exposed directly to formaldehyde vapor, the inconsistency of the results and the diversity of opinions which divide the users of these methods must be acknowledged. Also, a question which is being asked by hygienists is whether the apparatuses and processes currently in existence make it possible to produce sterilization or, more precisely, disinfection. Formaldehyde is generally employed in two ways, namely, either by depolymerizing paraformaldehyde by heating, or by injecting formol (an aqueous solution of formaldehyde at a strength of approximately 40%, with the addition of 5 to 10% of methanol) into a sterilizer which is, in addition, supplied with saturated steam at a pressure below atmospheric pressure. Although formaldehyde possesses a biocidal activity which is highly effective at concentrations above 5 mg per liter, and even 2 mg per liter, sterility is not always attained under these conditions of use because of the difficulty in controlling the sterilization parameters, particularly the gas concentration and relative humidity.

This random nature of sterilization with formaldehyde in the presence of steam has long been known as is evident from a study which was started in Britain in 1950 under the auspices of the Central Public Health Laboratory. In the discussion of experimental results it is stated that it was difficult to obtain reproducible results, that the effect of humidity was unclear and finally that disinfection with formaldehyde vapor is not to be attempted when any other process is available. Furthermore, the damaging role of water condensation has also been demonstrated.

Some manufacturers of apparatuses for low temperature sterilization have tried to avoid the problems due to water condensation by automatically purging condensates during the sterilization cycle. Others, aware of the wide variation in the concentration of gaseous formaldehyde during the sterilization cycle, have proposed repeated injections of formaldehyde in solution.

SUMMARY OF THE INVENTION

The present invention aims at providing a process and an apparatus for sterilization with a gaseous biocidal agent, in particular formaldehyde, which avoid the disadvantages of the techniques known at present.

A subject of the present invention is a process for sterilizing a material or an article by placing this material or this article in contact with a gas mixture containing at least one sterilizing agent produced by evaporating a liquid solution. The gas mixture containing at least one sterilizing agent is propelled in a circuit and brought into contact with the liquid solution which contains the sterilizing agent, in a dissolved, liquid and/or solid form, in a concentration which is sufficient to produce the desired concentration of the evaporated sterilizing agent.

Advantageously, the sterilizing agent is formaldehyde.

Preferably, the liquid solution is an aqueous solution of formaldehyde, if appropriate, containing other components such as inorganic or organic salts, or polyols such as glycerine, propylene glycol, ethylene glycol or polyoxyethylene glycols.

According to an advantageous embodiment of the process of the invention, the temperature of the gas mixture containing at least one sterilizing agent is between 20° and 100° C., and preferably between 55° and 65° C., and the material or the article to be sterilized is brought, before being placed in contact with this gas mixture, to a temperature close to or equal to that of this gas mixture.

To carry out the process, the material or the article to be sterilized is exposed to the gas mixture containing at least one sterilizing agent in a fluid-tight circuit, at least part of the circuit having been brought to the temperature of this gas mixture.

In this case, the operations of the process can be carried out at pressures above or below atmospheric pressure, and it is also possible to subject the gas mixture to pressure changes which are greater than the only pressure changes required for propelling the gas mixture containing at least one sterilizing agent in a circuit.

In particular, the operations of the process can be carried out with pressure drops down to approximately 1/20 of atmospheric pressure and pressure increases reestablishing atmospheric pressure or even up to 5 times the atmospheric pressure. In general, it is advantageous however to carry out the process at pressures which do not appreciably exceed atmospheric pressure.

According to an advantageous embodiment, the gas mixture enclosed in the chamber is subjected to least once to a pressure increase while the sterilization is being carried out by introducing a carrier gas or a carrier gas mixture into the chamber.

The term "carrier gas" is here understood as meaning a gaseous agent which, in itself, is inert from the point of view of sterilization, but whose addition to the gas mixture present in the chamber permits the total pressure therein to be increased. In particular, for this purpose, the carrier gas or carrier gas mixture is nitrogen or air or a mixture of these.

According to a particular embodiment of the process according to the invention, the material or the article to be sterilized is introduced into the chamber;
   the chamber is brought to a first subatmospheric pressure;
   steam is introduced producing an increase in pressure at a temperature, which is equal or close to that to which the material or the article is to be brought, until the intended temperature is attained, wherein partial suction of the steam and condensed water out of the chamber is continuously carried out;
   the admission of steam is interrupted;
   the chamber is brought to a reduced pressure until the water, which condensed during the introduction of steam, disappears;
   the chamber is brought into communication with the solution that is kept at a constant temperature equal to the temperature chosen for the gas mixture produced by evaporating this solution;
   the gas mixture present in the chamber is circulated and continuously brought back into contact with the solution;
   after the concentration of the sterilizing agent in the gas mixture present in the chamber has attained equilibrium with the solution, a carrier gas or a carrier gas mixture is introduced into the chamber, thus increasing the pressure therein until a total pressure is produced which is less than, equal to or greater than atmospheric pressure;
   the surface of the material or article is thus exposed for the time required to produce sterilization while the gas mixture present in the chamber is kept in circulation and continuously brought back into contact with the solution;
   the communication between the solution and the gas mixture present in the chamber is cut;
   the sterilizing agent present in the chamber is removed;
   the interior of the chamber is brought back to atmospheric pressure; and
   the material or article is withdrawn.

According to another embodiment of the process according to the invention, the material or the article to be sterilized is introduced into the chamber;
   the chamber is brought to a first subatmospheric pressure;
   steam is introduced producing an increase in pressure at a temperature, which is equal or close to that to which it is desired to bring the material or the article, until the intended temperature is attained, wherein partial suction of the steam and condensed water out of the chamber is continually produced;
   the introduction of steam remaining possible, a carrier gas or carrier gas mixture is introduced at least once into the chamber until a total pressure that is less than, equal to or greater than atmospheric pressure is produced, and after each introduction of carrier gas or carrier gas mixture the chamber is brought to a subatmospheric pressure less than that which was produced by introducing the carrier gas or carrier gas mixture;
   the admission of steam is interrupted;
   the chamber is brought to a reduced pressure until the water that condensed during the introduction of steam has disappeared;
   the chamber is placed in communication with the solution which is kept at a constant temperature equal to the temperature chosen for the gas mixture produced by evaporating this solution;
   the gas mixture present in the chamber is circulated and continuously brought back into contact with the solution;
   after the concentration of the sterilizing agent in the gas mixture present in the chamber has attained equilibrium with the solution, a carrier gas or carrier gas mixture is introduced into the chamber, thus increasing the pressure therein until a total pressure which is less than, equal to or greater than atmospheric pressure is obtained;
   the surface of the material or article is thus exposed for the time required to produce sterilization, while the gas mixture present in the chamber is kept in circulation and continuously brought back into contact with the solution;
   the communication between the solution and the gas mixture present in the chamber is cut;
   the sterilizing agent present in the chamber is removed;
   the interior of the chamber is brought back to atmospheric pressure; and
   the material or the article is withdrawn from it.

The process according to the invention can, however, also be carried out in a space in which there is a pressure close to atmospheric pressure, the only pressure differences in the various regions of this space, relative to atmospheric pressure, being those which become necessary for propelling the gas mixture present in this space in a circuit.

According to a particular embodiment of this process, the material or article to be sterilized is brought to a temperature equal or close to that at which its sterilization will be carried out;
   the material or article is subjected to a flow of a gas mixture containing at least one sterilizing agent obtained by evaporating the solution thereof, and this flow of gas mixture is continuously brought back into contact with the solution until sterilization of the material or article is produced; and
   the material or the article is subjected to a flow of sterile air to remove the sterilizing agent thereof.

Another subject of the invention is apparatuses for carrying out the process in its various embodiments.

In particular, a subject of the invention is an apparatus for sterilizing materials or articles by placing them in contact with a gas mixture containing at least one sterilizing agent produced by evaporating a liquid solution, this apparatus comprising a fluid-tight treatment chamber, with constant temperature control equipped with at least one door designed for loading materials or articles into the chamber and withdrawing them therefrom, this apparatus comprising in addition:

a sterilizing agent generator suitable for containing a solution of sterilizing agent and for evaporating the solution, which is maintained at a predetermined temperature by virtue of means of heating and/or cooling and means for temperature control;
   suitable means for introducing the gas mixture produced by the sterilizing agent generator into the chamber; for circulating the gas mixture present in the chamber and for continuously bringing it back into contact with the solution present in the sterilizing agent generator;

a circuit for admitting a carrier gas connected to the chamber and comprising a means for sterilizing a gas and a means for heating this gas at a constant temperature;

a steam generator connected, on the one hand, to the chamber and, on the other hand, to a water supply, and which is provided with a system for controlling the temperature and/or pressure; and suitable means for placing the sterilizing agent generator, the vacuum source, the admission circuit for carrier gas and the steam generator in communication with the chamber or cutting these communications.

According to an embodiment of this apparatus, the chamber is enclosed in a suitable enclosure for circulating a heat-carrying fluid and is connected to suitable means for ensuring the circulation, heating and temperature control of the heat-carrying fluid.

According to another embodiment of this apparatus, the chamber is a chamber of a plastic material which does not conduct electricity, which withstands the forces due to subatmospheric pressures, and which is equipped with electrical heating elements that are internal and/or embedded in the walls.

In an apparatus according to the invention the means for heating the gas at a constant temperature in the circuit for admitting carrier gas can be a heat exchanger heated by the steam generator.

According to an advantageous embodiment of the apparatus, the chamber is equipped with a temperature probe connected to a regulating device that causes the steam generator to continue to operate at least until the load has attained a predetermined temperature.

Another subject of the invention is an apparatus for sterilizing materials or articles by placing them in contact with a gas mixture containing at least one sterilizing agent produced by evaporating a liquid solution. This apparatus consists of a tunnel with constant temperature control provided with a suitable transporter for passing the materials or articles in succession therein, and which comprises, from its entry to its exit:

a preheating section equipped with suitable means for bringing the materials or articles to a predetermined temperature;

an entry protection section equipped with suitable means for producing a flow of air preheated to a predetermined temperature and directed so as to prevent the gaseous mixture present in the following section of the tunnel (sterilization section) from being capable of escaping through the tunnel entry;

a sterilization section equipped with a sterilizing agent generator suitable for containing a solution of the sterilizing agent and for evaporating the solution, which is maintained at a predetermined temperature by virtue of means for heating and/or cooling and means for temperature control, and which is also equipped with suitable means for introducing the gas mixture produced by the sterilizing agent generator into the sterilization section of the tunnel, circulating the gas mixture present in this section and continuously bringing this gas mixture back into contact with the solution present in the sterilizing agent generator; and an exit protection section provided with suitable means for producing a flow of sterile air directed so as to prevent the gaseous mixture present in the preceding section of the tunnel (sterilization section) from escaping through the exit of the tunnel.

In an apparatus according to the invention, the sterilizing agent generator can be fitted inside or outside the chamber (or tunnel).

According to another particular feature of apparatuses according to the invention, the steam generator maintains a steam pressure that is at most equal to atmospheric pressure.

According to another advantageous embodiment, the means for heating and temperature control of the sterilizing gas generator maintain the same temperature as in the steam generator.

The apparatuses according to the invention therefore comprise suitable means for introducing the gas mixture produced by the sterilizing agent generator into the sterilization space, for circulating the gas mixture present in this space and for continuously bringing it back into contact with the solution present in the sterilizing agent generator. According to a particular embodiment, these means comprise a liquid ring pump from which the liquid is withdrawn and brought continually back into the solution present in the sterilizing agent generator.

According to another particular embodiment, these means comprise a liquid jet pump from which the liquid, propelled by a liquid circulation pump, is withdrawn and brought continuously back into the solution present in the sterilizing agent generator.

The apparatuses according to the invention advantageously comprise means for programming the operations of the process.

The embodiments and particular features of operation described above offer various advantages, in particular:

The maintenance of a temperature of 60° C. in the whole apparatus avoids vapor pressures above atmospheric pressure and hence the safety accessories and measures required by autoclave and boilers, and enables the heat control circuits to be simplified;

The circulation of the chamber atmosphere using propulsion by a liquid ring pump aids constant temperature control by dissipating the pump energy in the ring liquid;

Pre-heating the carrier gas to the temperature of the steam generator ensures a low relative humidity in this gas and prevents cooling in the chamber so that there is no risk of water condensation;

The second optional door makes it possible to construct the apparatus as a lock installed between a septic zone and a sterile zone;

The manufacture of the chamber in a plastic material with a single heating wall is low in cost;

The circulation of the chamber atmosphere by continuously bringing it back into contact with the solution of a volatile sterilizing agent ensures the constancy of composition of the atmosphere by virtue of a constant re-establishing of equilibrium partial pressures;

The addition of a soluble carrier having a low vapor pressure to the solution of a volatile sterilizing agent makes it possible to affect the partial pressures without altering the temperature (at least within certain limits); and Maintenance of the steam generator at the temperature of the chamber avoids condensation in the chamber.

BRIEF DESCRIPTION OF THE DRAWINGS

Details and special features of the invention become apparent from the following description, given by way of non-limiting example, and with reference to the attached drawings in which.

DETAILED DESCRIPTION

Figure 1:
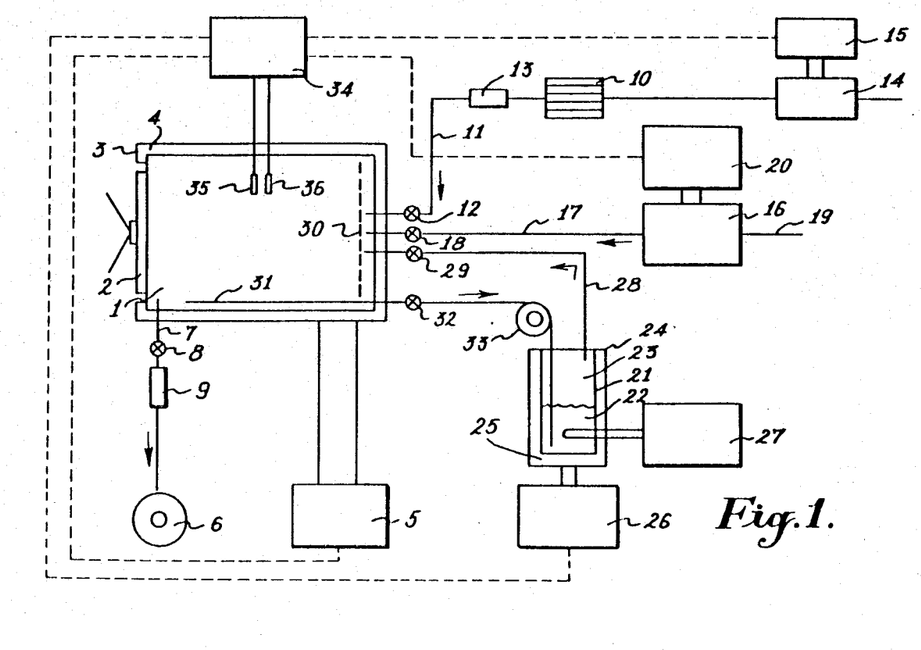
FIGS. 1 and 2 are diagrams showing two sterilization apparatuses according to the invention.

The sterilization apparatus shown diagrammatically in FIG. 1 comprises a treatment chamber 1 having a door 2 capable of being closed heremetically after the articles are loaded into the chamber. Door 2 is equipped with a heating means and means for controlling the heating. The chamber itself is enclosed in an enclosure 3 permitting the circulation of a heat-carrying fluid 4 and connected to means for the circulation, heating and control of the means of heating 5 at a variable temperature.

Chamber 1 is connected to a vacuum pump 6 by a conduit 7 having a valve 8 and a nonreturn valve 9. The chamber 1 is connected to a circuit for admitting a "carrier" gas comprising means 10 for sterilizing a gas, for example a sterilizing filter, a conduit 11 having a valve 12 and a non-return valve 13. Means 14 for heating the gas, controlled by means of control 15, can be fitted before the sterilization means 10. Heating means 14 can, if appropriate, produce the constant temperature control of the whole carrier gas conduit 11. This gas may be under pressure. The chamber 1 is connected to a steam generator 16 by a conduit 17 incorporating a valve 18. The generator 16 is connected to a water supply 19 and to a system for controlling the temperature and/or pressure 20.

Chamber 1 is connected to a sterilizing agent generator 21. The generator contains a liquid phase 22, a gaseous phase 23 and, if appropriate, a solid phase. It is enclosed in an enclosure 24 permitting the circulation of a heat-carrying fluid 25 and connected to means for circulating, heating and temperature control 26. The heating and the temperature of the liquid phase 22 and, if appropriate, a solid phase, are controlled by means 27. This heating system can form a part of the system for heating the chamber 1.

The gaseous phase 23 is circulated from the sterilizing agent generator 21 towards the chamber 1 through a conduit 28 having a valve 29, and is distributed into the chamber 1 by distribution panel 30. The gas 23 is recovered by the conduit 31 having the valve 32 and is driven by gas pump 33 through solution 22 before rejoining conduit 28. Conduits 28 and 31, valves 29 and 32 and gas pump 33 are thermostatic at the chosen sterilization temperature. Changes in temperature and pressure are controlled and regulated automatically by programmable control means 34, which records the temperature and the pressure by means of probes 35 and 36 and consequently controls the valves, vacuum pump 6, the heating elements and gas pump 33.

When the apparatus is operating, a liquid solution 22, which may be in contact with a solid phase containing a sterilizing agent capable of producing a gaseous phase 23 at the chosen sterilization temperature, is introduced into the gas generator 21. Heating means 5, 20, 26 and 27 are switched on. The load to be sterilized is introduced into the chamber 1 and the door 2 is closed. The chamber 1 is then automatically subjected, for a programmed time, to steam from the steam generator 16. Steam flow is controlled by valve 18, which is regulated so that the temperature in chamber 1 reaches the chosen sterilization temperature. Evacuation of the gases present in the chamber is simultaneously carried out by vacuum pump 6. In an alternative embodiment, a vacuum may be produced before introducing vapor. After the chosen time, the admission of steam is cut automatically by closing valve 18 while the vacuum pump 6 continues to operate for a pre-programmed time. Pressure in the chamber 1 reaches a low value. The load is hot and dry at that time. The operation of the vacuum pump 6 is interrupted automatically and valve 8 is closed. Valves 29 and 32 of the sterilizing agent generator 21 are opened automatically and gas pump 33 is started. The atmosphere in chamber 1 thus gradually fills with a mixture of sterilizing gas 23 originating from liquid phase 22 by evaporating the components. After a time, the concentration of the mixture of sterilizing gas in chamber 1 reaches equilibrium with the liquid phase 22 in the sterilizing agent generator 21, which is kept at a constant temperature, and is held at this level. The pressure in chamber 1 reaches a value equal to the pressure predominating before opening valves 29 and 32 of the sterilizing agent generator 21, and of the pressure due to the gaseous phase 23 originating from the liquid phase 22 in the sterilizing agent generator 21. The carrier gas inlet valve 12 is then automatically opened and the system for heating this gas 14 is simultaneously switched on until a pre-programmed total pressure is produced in chamber 1. This total pressure may be less than, equal to or greater than atmospheric pressure. The gaseous atmosphere in chamber 1 is then held unchanged during the period of reaction time required to produce total sterilization. Gas pump 33 continues to operate during this time and maintains equilibrium between sterilizing gaseous phase 23 and liquid phase 22. After the required time, gas pump 33 is stopped, and valves 29 and 32 are closed. A vacuum down to a determined pressure is then produced automatically by vacuum pump 6. The carrier gas heating circuit 14 is then switched on automatically and the carrier gas is admitted into chamber 1 up to a predetermined pressure. The cycle of evacuation and admission of carrier gas is repeated a sufficient number of times to ensure total removal of the sterilizing gas mixture from chamber 1. When the carrier gas is admitted, steam coming from steam generator 16 through conduit 17 may be automatically admitted with the carrier gas. Its temperature is controlled by probe 35 and control system 34. Finally, the carrier gas is automatically admitted into chamber 1 for a last time until atmospheric pressure is produced. Door 2 of chamber 1 is opened, the load is withdrawn and the chamber is ready to receive a new load.

It is self-evident that when steam generator 16 operates at the temperature to which the load to be sterilized is to be brought, it becomes unnecessary to control the action of valve 18, which results in a simplification of control.

Figure 2:
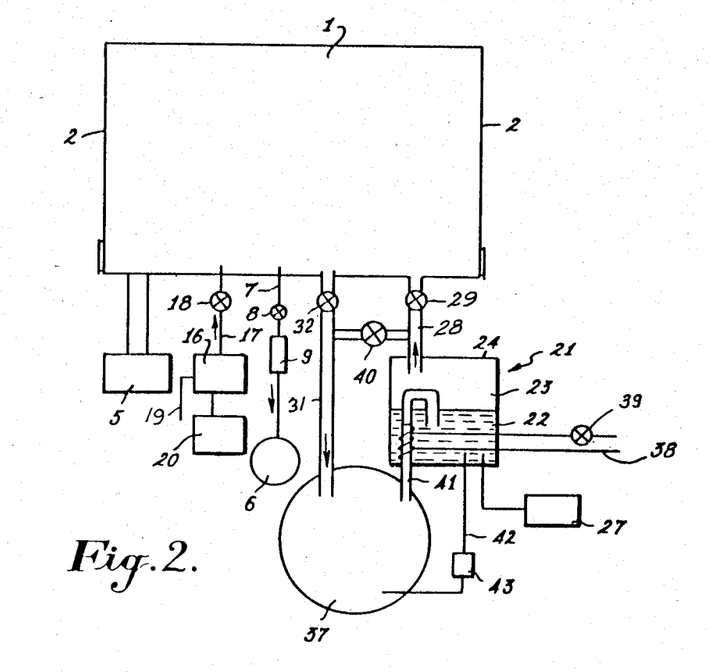

FIG. 2 illustrates another sterilization apparatus in which the components in common with those of the apparatus of FIG. 1 bear the same reference but are shown only when they are involved in the alternative embodiment.

The apparatus of FIG. 2 comprises a treatment chamber 1, which is a vessel of plastic material, comprising two doors 2 that can be closed after loading the articles into the chamber. Chamber 1 comprises heating elements 44 integral with the walls and means 5 for regulating heating at a variable temperature. Chamber 1 is connected to a vacuum system 6, 7, 8 and 9 and to circuit for admitting a "carrier" gas with their accessories, which are not shown and are similar to those of FIG. 1. Chamber 1 is connected to a steam generator 16 by a conduit 17 incorporating a valve 18. The generator 16 is connected to a water supply 19 and a system 20 for controlling the temperature and/or pressure. Chamber 1 is connected to a sterilizing agent generator 21, which contains a liquid phase 22, a gaseous phase 23 and, if appropriate, a solid phase. It is enclosed in an enclosure 24. Heating and the temperature of the liquid phase 22 and, if appropriate, a solid phase are controlled by a means of control 27 that operates as needed on cooling circuit 38 equipped with a valve 39. Gaseous phase 23 is circulated from the sterilizing agent generator 21 towards chamber 1 through a conduit 28 having a valve 29, and is propelled by a liquid ring pump 37. The gas 23 is recovered by conduit 31 having a valve 32. The mixture of gas and liquid leaving pump 37 returns to tank 24. Gas separated from liquid is returned to chamber 1 through conduit 28. A bypass conduit having a valve 40 between conduits 28 and 31 is used for starting pump 37 or for isolating the pump if need be.

The pump 37 is connected through a bent conduit 41 immersed in the liquid phase or solution 22, which is present in the sterilizing agent generator 21. The pump 37 is supplied with solution 22 by a conduit 42 equipped with a filter 43.

The apparatus of FIG. 2 otherwise operates substantially as that of FIG. 1.

The present invention can be carried out with various compositions of gas-producing liquids or mixtures of sterilizing gases, or with various carrier gases or carrier gas mixtures at various temperatures and pressures maintained for varying periods of time during the cycle. Moreover, the details of construction, fitting and arrangement of the apparatus described (for example, production of gaseous biocidal agent by continuous bubbling through the solution) may be modified, and a number of components may be replaced by other equivalent devices. For example, the heating circuits may be replaced by electrical resistors, or the circuits for heating the chamber and the gas generator may be combined into a single system.

The invention is illustrated by the following non-limiting Examples. In examples 1, 2 and 3, tests are carried out using known populations of spores of *Bacillus subtilis* (globigii) obtained by culturing and sporulating a reference biological indicator (American Sterilizer Co. "SPORDI"-trade name); these were deposited on polyethylene substrates and dried. They form biological indicators (B.I. in the text). In Example 4, the tests employ commercial B.I. or *B. subtilis* (globigii) with a paper substrate under the trade name AMSCO SPOR-DEX, Lot 646 GBL.

In the four Examples, the populations are subjected, packaged or not, to a treatment intended to sterilize them. They are recovered and cultured in a solution of Tryptic Soy Broth at a concentration of 30 g per liter for 14 days at 37° C. Examples 1, 2 and 3 were carried out in an apparatus such as shown diagrammatically in FIG. 1, equipped with a gas propeller of the ventilator type. Example 4 was carried out in an apparatus such as shown diagrammatically in FIG. 2 (with a liquid ring pump).

EXAMPLE 1

The sterilizing agent generator 21 is filled with a solution of 20.7% w/w of formaldehyde, 5.6% of methanol and 73.7% w/w of water. At 60° C., the gaseous phase obtained in the chamber 1 contains 9.8 mg per liter of gaseous formaldehyde and has a humidity of approximately 90%. A preliminary trial carried out in the absence of any obstacle to gas penetration showed that two minutes exposure to this gas mixture at 60° C. suffice to kill a population of $10^6$ spores. To test the sterilizing capacity of the invention when access to the spores is difficult, the microbial populations and their substrates were deposited in:

sealed polyethylene sachets (thickness 20 μm);

combined paper/plastic sealed sachets of the peelable type, such as used in hospital sterilization, (paper thickness 60 μm, thickness of the polyamide-polyethylene complex 60 μm);

10 ml and 2.5 ml syringes joined respectively to plasticized PVC tubing 3.5 m and 5 m in length and 2 mm in internal diameter;

plasticized PVC tubing 5 m in length and 2 mm in internal diameter connected at one end to a capsule of internal volume 1.1 ml containing the biological indicators (this system is called a "Helix type catheter"); and 20 ml polyethylene vials fitted with stoppers unscrewed a quarter turn.

For these trials, the following sterilization cycle was applied after equilibrating the means of heating 5, 15, 26 and 27 at 60° C.:

(1) an initial evacuation down to 0.1 bar (time of pumping: 0.5 min);

(2) heating the articles in saturated steam of 60° C. (time: 5 min);

(3) drying the articles and the chamber walls under reduced pressure until a residual pressure of 0.05 bar is obtained (time: 5 min);

(4) production of the sterilization gaseous phase (time: 10 min);

(5) admission of air up to atmopsheric pressure (time: 0.5 min);

(6) sterilization proper (time: from 20 to 30 min);

(7) removal of the gas under vacuum, alternating with admissions of steam and air (time: 10 min); and (8) a return to atmospheric pressure (0.5 min).

Figure 3:
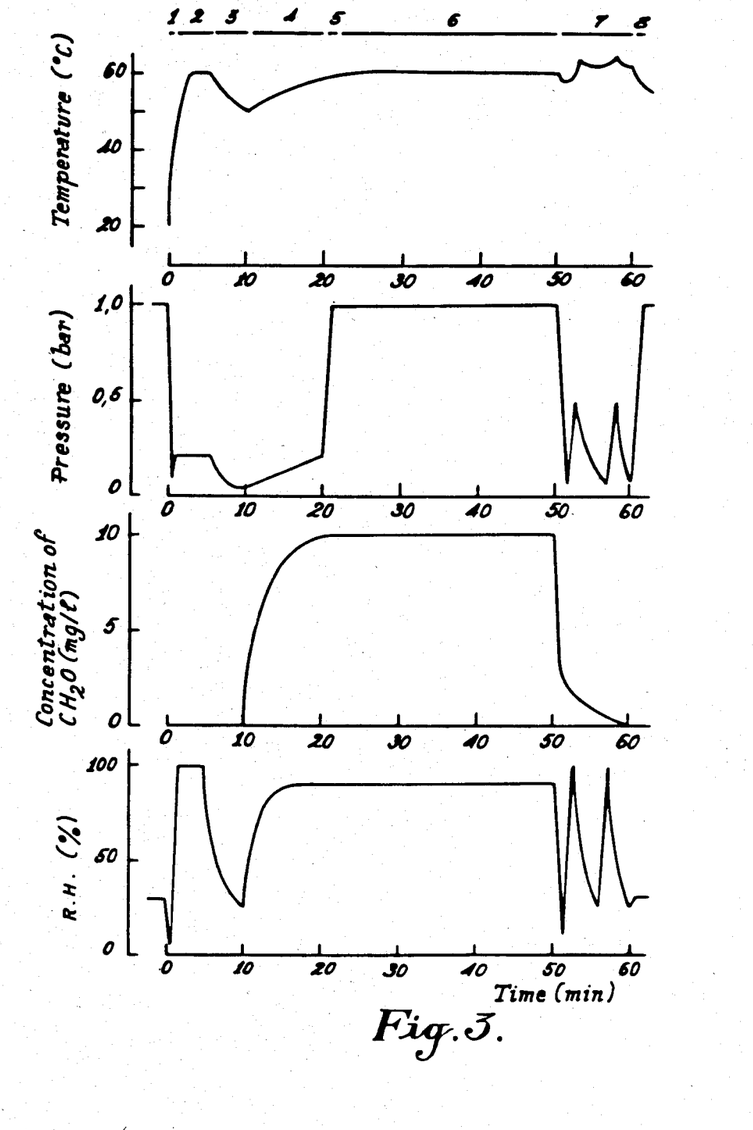
FIGS. 3, 4, 5, and 6 illustrate changes in the temperature, pressure, concentration of gaseous formaldehyde and relative humidity during sterilization cycles carried out in Examples 1, 2, 3 and 4, respectively.

Total duration: from 50 to 60 minutes. The change in the temperature, total pressure in the chamber, concentration of gaseous formaldehyde and relative humidity in the chamber, as a function of time, is shown in FIG. 3.

In order to verify whether the formaldehyde residues which may be present in the polyethylene substrate of the indicators can inhibit the growth of germs surviving the sterilization treatment, a comparative germ growth culture was repeated 10 times. An indicator which had been subjected to autoclaving with formaldehyde and an indicator which had not undergone any formaldehyde treatment were introduced into an identical tube containing the culture medium. A bacterial growth was observed immediately in each of the 10 tubes demonstrating that the residue of formaldehyde which may be present after treatment is insufficient to inhibit the growth of germs which might have failed to be destroyed by autoclaving with formaldehyde. The results of the sterilization tests are shown in Table I.

EXAMPLE 2

The same liquid phase as in Example 1 is employed in the sterilizing agent generator 21. At 40° C., the gaseous phase produced in the chamber 1 contains 5.1 mg per liter of gaseous formaldehyde and has a relative humidity of approximately 95%.

To test the sterilizing capacity of the invention when access to the spores is difficult, the microbial populations and their substrates were deposited in "Helix" type catheters described in Example 1.

Figure 4:
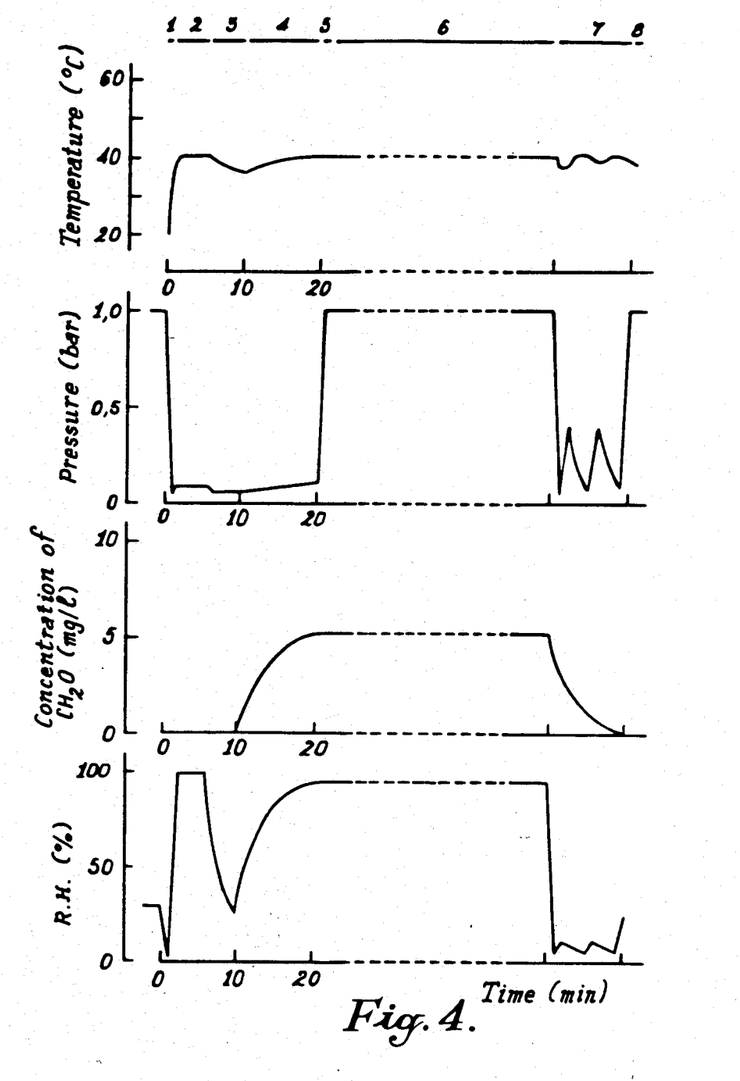

The change in the parameters of temperature, pressure, formaldehyde concentration and relative humidity in chamber 1 is given in FIG. 4. This means of heating 5, 15, 26 and 27 were thermostated at 40° C. The results of the sterilization tests are presented in Table II.

TABLE I

| Material containing the biological indicators | Number of B.I. and population | Sterilization time (min.) (step 6) | Number of sterile B.I./total number of B.I. |
|---|---|---|---|
| Polyethylene sachet | $8 \times 10^{5.6}$ | 30 | 16/16 |
|  | $8 \times 10^{6.5}$ | 30 |  |
| Heat-sealed paper-plastic sachet | $4 \times 10^{6.5}$ | 30 | 43/43 |
|  | $19 \times 10^{6.3}$ | 30 |  |
|  | $20 \times 10^{6.3}$ | 30 |  |
| Polyethylene vials (stopper open one quarter turn) | $3 \times 10^{6.5}$ | 30 | 16/16 |
|  | $13 \times 10^{6.3}$ | 30 |  |
| 10-ml syringe | $1 \times 10^{5.6}$ | 30 | 8/8 |
|  | $1 \times 10^{6.3}$ | 30 |  |
|  | $1 \times 10^{6.3}$ | 20 |  |
|  | $1 \times 10^{6.2}$ | 20 |  |
| 2.5-ml syringe | $2 \times 10^{5.6}$ | 30 | 9/9 |
|  | $1 \times 10^{6.3}$ | 30 |  |
|  | $1 \times 10^{6.3}$ | 20 |  |
|  | $5 \times 10^{6.2}$ | 20 |  |
| "Helix" type catheter | $16 \times 10^{6.3}$ | 20 | 38/38 |
|  | $22 \times 10^{6.2}$ | 20 |  |

TABLE II

| Material containing the biological indicators | Number of B.I. and population | Sterilization time (min) | Number of sterile B.I./total number of B.I. |
|---|---|---|---|
| "Helix" type catheter | $22 \times 10^{6.2}$ | 30 | 0/22 |
|  | $22 \times 10^{6.2}$ | 60 | 6/22 |
|  | $22 \times 10^{6.2}$ | 120 | 13/22 |
|  | $22 \times 10^{6.2}$ | 240 | 22/22 |

EXAMPLE 3

The sterilizing agent generator 21 is filled with a solution containing 20.3% of formaldehyde, 5.5% w/w of methanol, 29.2% w/w of water and 45.1% w/w of propylene glycol. At 60° C., the gaseous phase produced in the chamber contains 12.1 g per liter of gaseous formaldehyde and has a relative humidity of approximately 70%.

Figure 5:
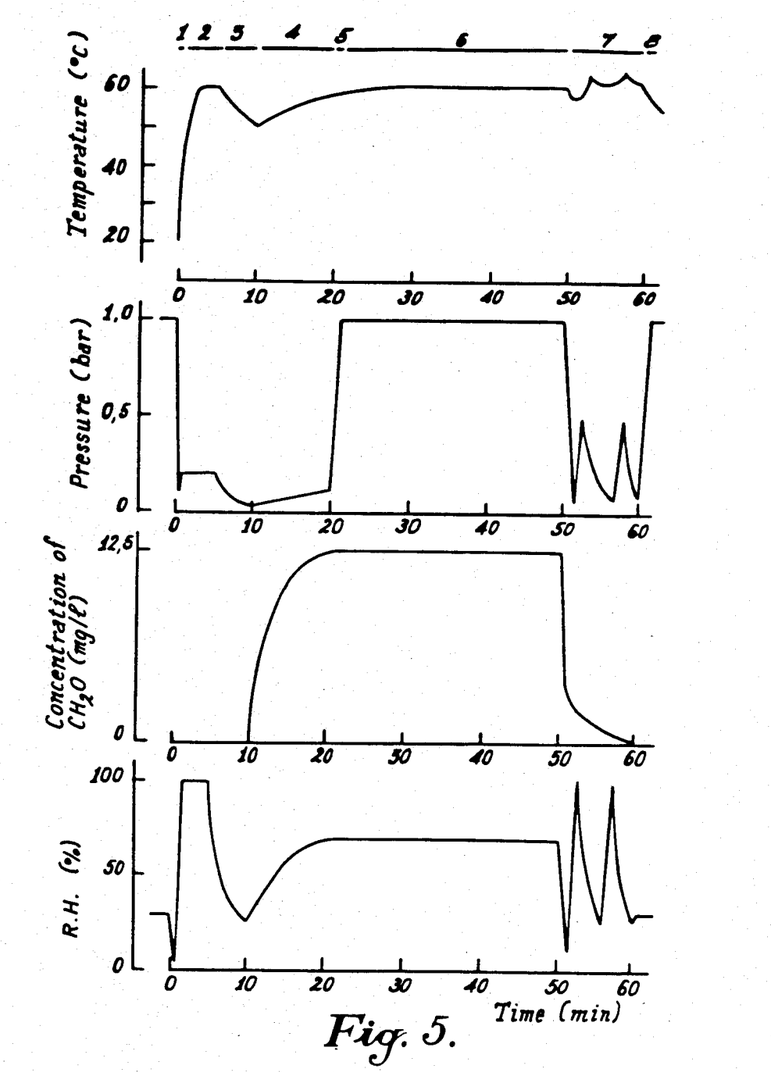

To test the sterilizing capacity of the invention when access to the spores is difficult, the microbial populations and their substrates were deposited in catheters of the "Helix" type described in Example 1. The change in the parameters of temperature, pressure, formaldehyde concentration and humidity in the chamber is shown in FIG. 5. The means of heating 5, 15, 26 and 27 were thermostated at 60° C. The results of the sterilization tests are as follows:

TABLE III

| Number of B.I. and population | Sterilization time (min) (step 6) | Number of sterile B.I./total number of B.I. |
|---|---|---|
| $17 \times 10^{6.2}$ | 30 | 17/17 |

EXAMPLE 4

The tank 24 of the sterilizing agent generator 21 is partially filled with a solution containing 20.3% w/w of formaldehyde, 5.5% w/w of methanol, 29.2% w/w of water and 45.1% w/w of propylene glycol, and feeds, by means of a conduit, the liquid ring pump 37. At 60° C., the gaseous phase obtained in the chamber contains 17.35 mg per liter of gaseous formaldehyde and has a relative humidity of approximately 70%. To test the sterilizing capacity of the invention when the spores are in an environment capable of significant absorption of the gaseous formaldehyde and steam, the microbial populations and their polyethylene substrates were deposited in combined paper/plastic sachets of a peelable type, such as are employed in hospital sterilization, and sealed. Commercial biological indicators with a paper substrate were employed in the original paper packaging (AMSCO SPORDEX, Lot 646 GBL). The wrapped indicators were then deposited in the middle of a stack of 30 pieces of cotton, 65×70 cm, each folded three times. The specimen stack weighed 3 kg. The whole was wrapped in a sterilization paper, and is called a "Bowie Test." The temperature of the steam generator 16 was fixed at 60° C.

For these trials, the following sterilization cycle was employed after equilibrating at 60° C. the means of heating 5 and 15:

(1) an initial vacuum down to 0.1 bar (time of pumping: 0.5 min);

(2) heating the articles in saturated steam until a temperature of 60° C. is obtained in the middle of the stack of cloths (time: approximately 15 min);

(2') admission of air up to atmospheric pressure (time: 0.5 min), an evacuation of the atmosphere from the chamber down to 0.3 bar (time: 0.5 min). This is repeated 3 times in all, the valve 18 remaining open;

(3) drying the load and the walls under vacuum until a residual pressure of 0.1 bar is obtained, the valve 18 being closed (time: 5 min), this concluding the preconditioning;

(4) production of the sterilization gaseous phase (time: 10 min);

(5) admission of air until a pressure of 0.95 bar is obtained (time: 0.5 min) with the gas pump 37 stopped;

(6) sterilization proper (time: 20 min), this completing the sterilization phase;

(7) an evacuation of the gas under vacuum, the valve 18 being opened at least once if necessary, alternating with admission of air (time: 5 min); and (8) a return to atmospheric pressure (time: 0.5 min), this completing the postconditioning (total duration: 60 min).

Figure 6:
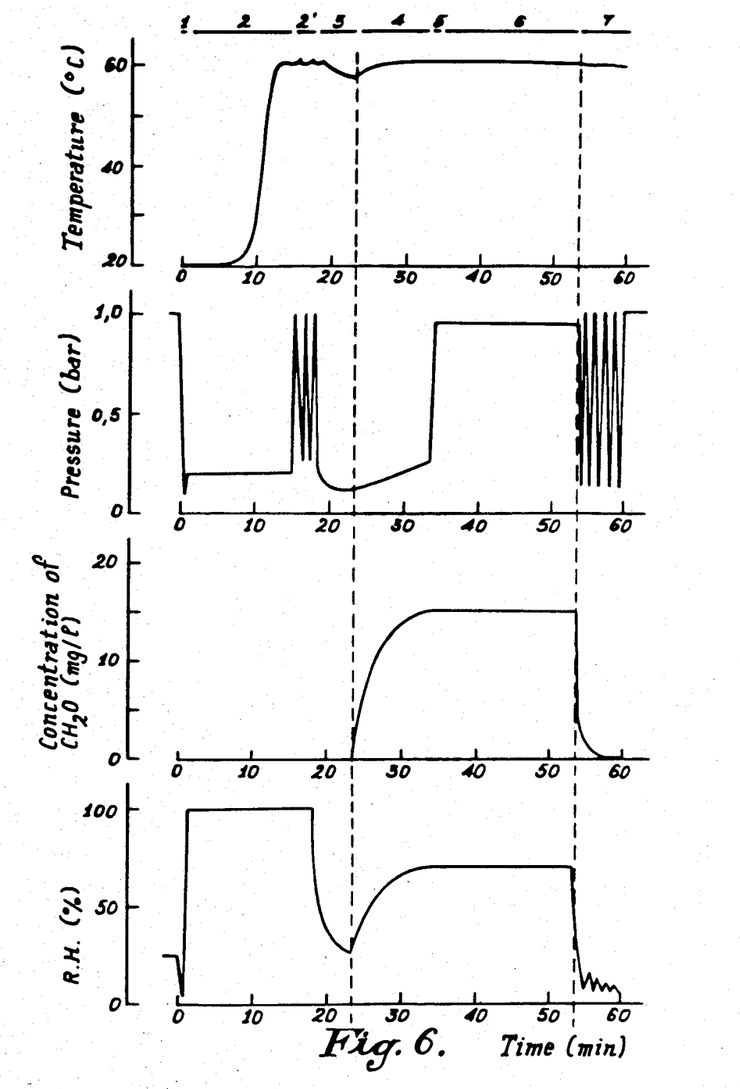

The change in the temperature, total pressure in the chamber, concentration of gaseous formaldehyde and relative humidity in the chamber, as a function time, is shown in FIG. 6.

The results of the sterilization tests are shown in Table IV.

TABLE IV

| Material containing the biological indicators | Number of B.I. and population | Sterilization time (min) (step 6) | Number of sterile B.I./ total number of B.I. |
| --- | --- | --- | --- |
| Polyethylene | $35 \times 10^{5.9}$ | 20 | 35/35 |
| Paper | $13 \times 10^{5.7}$ | 20 | 13/13 |

What is claimed is:

1. A process for sterilizing a material or an article comprising the following steps in combination:

introducing the material or article to be sterilized into a chamber;

evacuating the chamber to a subatmospheric pressure;

admitting steam into the chamber to produce an increase in pressure until a temperature is attained within the chamber which is close to the desired sterilization temperature, while simultaneously maintaining a suction of steam and condensed water out of the chamber;

interrupting the admission of steam;

evacuating the chamber to a reduced pressure until the water which has condensed during the admission of steam has been removed;

bringing the chamber into communication with a gaseous phase containing formaldehyde to produce a gas mixture comprising the chamber atmosphere and the gaseous phase, said gaseous phase produced by evaporating an aqueous solution of formaldehyde which is kept at a constant temperature equal to the temperature desired for sterilization;

circulating the gas mixture from the chamber to the aqueous solution so that the gas mixture is continuously brought back into contact with the aqueous solution;

after the concentration of formaldehyde in the gas mixture has attained equilibrium with the aqueous solution, introducing a carrier gas into the chamber to increase pressure therein until a total pressure at about atmospheric pressure is produced and maintained therein;

exposing the surface of the material or article within the chamber for a time required to produce sterilization under the condition of constant temperature, pressure, formaldehyde concentration and relative humidity by continuing to keep the gas mixture in circulation and continuously bringing it back into contact with the aqueous solution, maintaining the pressure within the chamber at about atmospheric pressure, and maintaining the temperature of the gas mixture at the desired sterilization temperature;

cutting off communication between the aqueous solution and the gas mixture present in the chamber;

removing the formaldehyde present in the chamber by evacuation;

bringing the interior of the chamber back to atmospheric pressure by introduction of said carrier gas; and withdrawing the material or article.

2. A process according to claim 1, characterized in that the sterilization temperature of the gas mixture is within the range of 20° to 100° C.

3. A process according to claim 1, wherein the carrier gas is selected from the group consisting of nitrogen, air or mixtures thereof.

4. A process according to claim 1 in which the aqueous solution of formaldehyde contains a polyol.

5. A process according to claim 4 in which the polyol is selected from the group consisting of glycerol, propylene glycol, ethylene glycol or polyoxyethylene glycol.

6. A process for sterilizing a material or an article comprising the following steps in combination:

introducing the material or article to be sterilized into a chamber;

evacuating the chamber to subatmospheric pressure;

admitting steam into the chamber to produce an increase in pressure until a temperature is attained within the chamber which is close to the desired sterilization temperature, while simultaneously maintaining a suction of steam and condensed water out of the chamber;

introducing a carrier gas at least once into the chamber to produce an increase in pressure, and after the at least one introduction of carrier gas, evacuating the chamber to a subatmospheric pressure which is less than that which was produced by introducing the carrier gas;

interrupting the admission of steam;

evacuating the chamber to a reduced pressure until the water which has condensed during the introduction of steam has been removed;

bringing the chamber into communication with a gaseous phase containing formaldehyde to produce a gas mixture comprising the chamber atmosphere and the gaseous phase, said gaseous phase produced by evaporating an aqueous solution of formaldehyde which is kept at a constant temperature equal to the temperature desired for sterilization;

circulating the gas mixture "present in the chamber and" has been replaced by from the chamber to the aqueous solution so that the gas mixture is continuously brought back into contact with the aqueous solution;

after the concentration of formaldehyde in the gas mixture has attained equilibrium with the aqueous solution, introducing a carrier gas into the chamber, to increase the pressure therein until a total pressure at about atmospheric pressure is produced and maintained therein;

exposing the surface of the material or article within the chamber for a time required to produce sterilization under the conditions of constant temperature, pressure, formaldehyde concentration and relative humidity by continuing to keep the gaseous phase in circulation and continuously bringing it back into contact with the aqueous solution, maintaining the pressure within the chamber at about atmospheric pressure, and maintaining the temperature of the gas mixture at the desired sterilization temperature;

cutting off communication between the aqueous solution and the gas mixture present in the chamber;

removing the formaldehyde present in the chamber by evacuation;

bringing the interior of the chamber back to atmospheric pressure by introduction of said carrier gas and withdrawing the material or article.

* * * * *